United States Patent [19]

Rapaport

[11] Patent Number: 5,730,991
[45] Date of Patent: Mar. 24, 1998

[54] HOME SKIN PEEL COMPOSITION FOR PRODUCING HEALTHY AND ATTRACTIVE SKIN

[75] Inventor: Jeffrey Rapaport, Fort Lee, N.J.

[73] Assignee: Dermatology Home Products, Inc., Fort Lee, N.J.

[21] Appl. No.: 609,607

[22] Filed: Mar. 1, 1996

Related U.S. Application Data

[63] Continuation of Ser. No. 70,559, Jun. 1, 1993, Pat. No. 5,505,948.

[51] Int. Cl.$^6$ .............................. A61K 6/00; A61K 7/00
[52] U.S. Cl. .................. 424/401; 424/489; 424/446; 424/402
[58] Field of Search .................... 424/401, 489, 424/78.01, 78.02, 78.03; 514/2

[56] References Cited

U.S. PATENT DOCUMENTS

| | | | |
|---|---|---|---|
| Re. 28,957 | 9/1976 | Drelich et al. | 427/331 |
| 3,706,595 | 12/1972 | Drelich et al. | 117/38 |
| 3,778,341 | 12/1973 | Plummer et al. | 162/125 |
| 3,879,537 | 4/1975 | Van Scott et al. | 424/311 |
| 3,920,835 | 11/1975 | Van Scott et al. | 424/311 |
| 3,984,566 | 10/1976 | Van Scott et al. | 424/283 |
| 3,988,470 | 10/1976 | Van Scott et al. | 424/283 |
| 4,021,572 | 5/1977 | Van Scott et al. | 424/317 |
| 4,035,513 | 7/1977 | Kumano | 424/359 |
| 4,054,649 | 10/1977 | Cariel | 424/195 |
| 4,105,783 | 8/1978 | Yu et al. | 424/283 |
| 4,124,720 | 11/1978 | Wenmaekers | 424/278 |
| 4,177,260 | 12/1979 | Wajaroff | 424/71 |
| 4,195,077 | 3/1980 | Marsh et al. | 424/70 |
| 4,197,316 | 4/1980 | Yu et al. | 424/317 |
| 4,234,599 | 11/1980 | Van Scott et al. | 424/279 |
| 4,246,261 | 1/1981 | Van Scott et al. | 424/240 |
| 4,283,386 | 8/1981 | Van Scott et al. | 424/70 |
| 4,287,214 | 9/1981 | Van Scott et al. | 424/346 |
| 4,294,852 | 10/1981 | Wildnauer et al. | 424/317 |
| 4,309,469 | 1/1982 | Varona | 428/74 |
| 4,341,213 | 7/1982 | Cohen | 128/284 |
| 4,363,815 | 12/1982 | Yu | 424/274 |
| 4,368,187 | 1/1983 | Flom et al. | 424/81 |
| 4,380,549 | 4/1983 | Van Scott et al. | 424/317 |
| 4,424,234 | 1/1984 | Alderson et al. | 424/317 |
| 4,478,853 | 10/1984 | Chaussee | 424/358 |
| 4,505,925 | 3/1985 | Elslager et al. | 514/405 |
| 4,514,385 | 4/1985 | Damani et al. | 424/81 |
| 4,518,789 | 5/1985 | Yu et al. | 560/105 |
| 4,537,776 | 8/1985 | Cooper | 514/424 |
| 4,557,934 | 12/1985 | Cooper | 424/128 |
| 4,569,935 | 2/1986 | Rosenberg et al. | 514/252 |
| 4,588,590 | 5/1986 | Bernstein | 424/195.1 |
| 4,603,146 | 7/1986 | Kligman | 514/559 |
| 4,608,370 | 8/1986 | Aronsohn | 514/159 |
| 4,695,452 | 9/1987 | Gannis et al. | 424/59 |
| 4,719,226 | 1/1988 | Otsuka et al. | 514/449 |
| 4,727,060 | 2/1988 | Buhlmayer et al. | 514/18 |
| 4,735,798 | 4/1988 | Bernstein | 424/61 |
| 4,738,848 | 4/1988 | Yoshida et al. | 424/448 |
| 4,800,197 | 1/1989 | Kowcz et al. | 514/162 |
| 4,824,865 | 4/1989 | Bowser et al. | 514/558 |
| 4,830,854 | 5/1989 | Copelan | 424/445 |
| 4,837,378 | 6/1989 | Borgman | 424/81 |
| 4,839,161 | 6/1989 | Bowser et al. | 424/59 |
| 4,844,098 | 7/1989 | Mitchen | 128/765 |

(List continued on next page.)

FOREIGN PATENT DOCUMENTS

| | | |
|---|---|---|
| 748349-A | 8/1962 | Canada . |
| 1074824-A | 4/1993 | China . |
| 129003-A | 12/1984 | European Pat. Off. . |
| 0599819 A3 | 11/1987 | European Pat. Off. . |
| 273202-A | 7/1988 | European Pat. Off. . |
| 297436-A | 1/1989 | European Pat. Off. . |
| 0327327 A3 | 2/1989 | European Pat. Off. . |
| 4135528-A | 2/1991 | European Pat. Off. . |
| 588379-A2 | 3/1994 | European Pat. Off. . |
| 3421293-A | 12/1985 | Germany . |
| 69008916-B | 12/1966 | Japan . |
| 50040896-A | 4/1975 | Japan . |

(List continued on next page.)

OTHER PUBLICATIONS

Penders, Paul: brochure "Herbal Citrus Fruit Exfoliant", Paul Penders, 1340 Commerce St., Petaluma, CA 94954.
"Fresh & New", advertising brochure.
VanDongen, Susan: "A Fountain of Youth", *Shopper's Guide-3*, Jan. 15, 1993.
"Reviva Labs—Beauty News", Edition 17, 1993, Reviva Labs.
"Alpha Hydrox—Face Cream", advertisement with $1.00 coupon.
*Merck Index*, a) "4362. Gycolic Acid", p. 646, b) 8190. Salicylic Acid, p. 1200, c) 213. Alcohol Denatured, p. 35, d) 58—Acetone, p. 10.
"Glyderm Program": advertising catalog, Glyderm, Inc., Southfield, MI 48076.
Murad, Dr. Howard: "A Primer on Glycolic Acid", Dermascope, Dallas, TX 75205, Mar./Apr. 1993.
New Jersey Dept. of Health: "Acetone" *Hazardous Substance Fact Sheet*, CAS #67-64-1, DOT #UN1090, Feb. 1989.
Kechigian, Paul: "Nail Polish Removers: Are They Harmful?", W.B. Saunders Co. 1991.
"Duofilm"—Steifel Laboratories, Inc., Coral Gables, FL, *Physician's Desk Reference*, 1985, p. 2035.

*Primary Examiner*—Joseph L. Schofer
*Assistant Examiner*—William E. Benston, Jr.
*Attorney, Agent, or Firm*—Alfred M. Walker

[57] ABSTRACT

A composition, a method, and a kit are provided for at-home chemical skin peeling, which is gentle in that the concentrations of the active skin peeling ingredients is far lower than that used in dermatologists' or aestheticians' offices. The composition of the present invention is designed to be used daily over a period of weeks to produce the same or a superior result compared to superficial or light chemical peels available in a professional setting alone and superior to any product, method, kit or composition for home use in skin peeling.

11 Claims, No Drawings

U.S. PATENT DOCUMENTS

| | | | |
|---|---|---|---|
| 4,847,270 | 7/1989 | Bender et al. | 514/333 |
| 4,874,361 | 10/1989 | Obagi | 604/20 |
| 4,877,805 | 10/1989 | Kligman | 514/381 |
| 4,883,669 | 11/1989 | Chien et al. | 424/448 |
| 4,891,227 | 1/1990 | Thaman et al. | 424/443 |
| 4,891,228 | 1/1990 | Thaman et al. | 424/443 |
| 4,931,591 | 6/1990 | Buhlmayer et al. | 564/165 |
| 4,942,162 | 7/1990 | Rosenberg et al. | 514/252 |
| 4,956,184 | 9/1990 | Kross | 424/661 |
| 4,956,347 | 9/1990 | Ban et al. | 514/54 |
| 4,963,557 | 10/1990 | Badger et al. | 514/278 |
| 4,963,591 | 10/1990 | Fourman et al. | 514/944 |
| 4,980,378 | 12/1990 | Wong et al. | 514/785 |
| 5,049,381 | 9/1991 | Schultz et al. | 424/401 |
| 5,061,700 | 10/1991 | Dow et al. | 514/169 |
| 5,063,062 | 11/1991 | Greenspan et al. | 424/443 |
| 5,073,372 | 12/1991 | Turner et al. | 424/401 |
| 5,086,060 | 2/1992 | Haley et al. | 514/294 |
| 5,091,171 | 2/1992 | Yu et al. | 424/642 |
| 5,091,379 | 2/1992 | Aungst | 514/159 |
| 5,093,360 | 3/1992 | Yu et al. | 514/463 |
| 5,100,652 | 3/1992 | Kross et al. | 424/53 |
| 5,110,603 | 5/1992 | Rau | 424/466 |
| 5,133,967 | 7/1992 | Smith | 424/401 |
| 5,134,150 | 7/1992 | Bender et al. | 514/318 |
| 5,134,163 | 7/1992 | Kligman | 514/559 |
| 5,140,047 | 8/1992 | Adams et al. | 514/575 |
| 5,145,858 | 9/1992 | Adams et al. | 514/318 |
| 5,153,230 | 10/1992 | Jaffery | 514/847 |
| 5,154,174 | 10/1992 | Hawlina | 128/639 |
| 5,164,413 | 11/1992 | Willis | 514/557 |
| 5,174,475 | 12/1992 | Day et al. | 222/144.5 |
| 5,252,332 | 10/1993 | Goldstein | 424/402 |
| 5,258,391 | 11/1993 | Van Scott et al. | 514/529 |
| 5,270,344 | 12/1993 | Herman | 514/725 |
| 5,292,530 | 3/1994 | McCrea et al. | 424/66 |
| 5,326,790 | 7/1994 | Thornfeldt | 514/784 |
| 5,364,879 | 11/1994 | Herman | 514/452 |
| 5,384,134 | 1/1995 | Kross et al. | 424/661 |
| 5,385,938 | 1/1995 | Yu et al. | 514/557 |
| 5,389,677 | 2/1995 | Yu et al. | 514/557 |
| 5,407,958 | 4/1995 | Atkins et al. | |
| 5,411,734 | 5/1995 | Vargas et al. | 424/401 |
| 5,420,106 | 5/1995 | Parab | 514/2 |
| 5,425,938 | 6/1995 | Crotty et al. | |
| 5,441,740 | 8/1995 | Ozlen | |
| 5,470,880 | 11/1995 | Yu et al. | 514/574 |
| 5,505,948 | 4/1996 | Rapport | 424/401 |
| 5,593,680 | 1/1997 | Bara et al. | 424/401 |

FOREIGN PATENT DOCUMENTS

| | | |
|---|---|---|
| 56070018-A | 6/1981 | Japan . |
| 07138142-A | 5/1995 | Japan . |
| 07165554-A | 6/1995 | Japan . |
| 87343-A | 8/1985 | Romania . |
| 822824-B | 4/1981 | U.S.S.R. . |
| 1779373-A | 12/1992 | U.S.S.R. . |
| 1785684A1 | 1/1993 | U.S.S.R. . |
| WO 95/20403 | 9/1985 | WIPO . |
| WO 9207587-A1 | 5/1992 | WIPO . |
| WO 93/25186 | 12/1993 | WIPO . |
| WO 94/02674 | 2/1994 | WIPO . |
| WO 94/06440 | 3/1994 | WIPO . |
| WO 9503032-A1 | 2/1995 | WIPO . |

HOME SKIN PEEL COMPOSITION FOR PRODUCING HEALTHY AND ATTRACTIVE SKIN

This application is a continuation of application Ser. No. 08/070,559, filed Jun. 1, 1993, now U.S. Pat. No. 5,505,948.

FIELD OF THE INVENTION

The present invention relates to topical compositions and methods for producing healthy, youthful, attractive, natural looking human skin, and for addressing certain problem skin conditions, including aging skin, dry skin, photo aged skin, i.e., sun damaged skin, hyperpigmentation [brown and black blotches] or darkly pigmented skin [e.g. natural skin pigmentation of black persons], acne, eczema, thin skin, which occurs commonly in Caucasian women between the ages of 25 and 40, where skin thickness is reduced, sensitive skin and composite dry-oily skin also known as T-zone oily skin.

Alpha hydroxy acids, such as glycolic and lactic acids, for example, when topically applied in a suitable pharmaceutical vehicle have the ability to (a) remove the thickened horny layer of the epidermis; (b) improve the barrier function of the skin, i.e., the ability of skin to hold water in and protect against invasion of harsh external elements; (c) increase or stimulate the natural production of ground substance, comprising collagen, natural dermal elastic substances and proteins; and (d) generally increase the strength and integrity of the skin. The present invention accomplishes all of the foregoing advantages, but in a novel, more effective fashion employing novel means for application. The present invention is a chemical peel for at home use and which can be left on the skin—and thus it has the foregoing advantages.

In the present invention, an important novel feature arises from low concentrations of a synergistic combination of peeling agents which peel and/or exfoliate the skin. The combination includes acetone with glycolic, lactic and salicylic acids. However, because glycolic and lactic acids are humectants, the peeling/exfoliating combination is left on the skin and acts as a moisturizing skin treatment. Another important novel feature is the use of acetone in low concentrations as both a skin degreaser and as a peeling agent.

Acetone in high concentrations has been shown to cause skin blistering, and has been shown to cause fingernails to crack. In lower concentrations, acetone effects peeling of the skin. It is used in two steps of the present invention—to degrease the skin in preparation for topically applying peeling agents, and then as a peeling agent itself in a synergistic combination of low concentration glycolic and lactic acids. The peeling effect of the acetone begins when it is applied as a degreaser and continues with the subsequent application of peeling agents which contain acetone, as more fully described below.

BACKGROUND OF THE INVENTION

It is known that the epidermal, or outer layers of human skin can be caused to peel by applying preparations to remove dead skin and to wound underlying living skin tissue. The beneficial result of such skin peeling is that when underlying layers of skin are exposed, the underlying skin is relatively free of age lines, superficial wrinkles, acne scarring, dryness, pigment spots, aging spots, acne lesions, and, with an appropriate topical composition, without the same relative degree of hyperpigmentation as compared to the same skin before a topical peeling composition was applied.

Removing old, dead surface skin cells exposes younger underlying skin tissue, which looks more youthful in part because it is smoother and reflects light more readily, thus rendering a "healthy glow" appearance. Removal of the buildup of dead skin cells is critical to producing younger-looking skin because the dead cell buildup is partly responsible for the rough, dry look associated with superficial fine lines, crow's feet, wrinkles and the like.

Chemical skin peeling is closely related to the art of skin exfoliation. Chemical skin peeling involves chemically contacting and wounding the living skin tissue found below the surface layer of dead skin cells. To accomplish this, the surface dead cells must be either removed or penetrated by the chemical peeling agents. The agents loosen the bonds between dead skin cells and underlying living tissue and stimulate the living skin tissue to form new collagen and to metabolically remove dead cells and detritus. In contrast, skin exfoliation involves only contact with and removal of all or a portion of the surface dead skin, without affecting the underlying living skin tissue. The difference between skin peeling and skin exfoliation is thus one of degree rather than of kind.

Peeling and exfoliation of the skin may be accomplished with the same chemical agents, and exfoliation is a more gentle skin treatment process than chemical peeling, since exfoliation removes only dead skin cells from the skin surface and does not wound living cells.

DISCUSSION OF THE PRIOR ART

Various attempts have been made to utilize alpha-hydroxy acids, such as glycolic acid, in skin care products, as noted in U.S. Pat. Nos. 3,879,537, 3,920,835, 3,984,566, 3,988,470, 4,021,572, 4,105,783, 4,197,316, 4,234,599, 4,246,261, 4,363,815, 4,380,549, and 4,363,815 of Van Scott and Yu. Glycolic acid has been specifically described as an agent to loosen bonds between dead and like skin cell layers, as noted in M. Murad, "A Primer on Glycolic Acid,"March/April, 1993, Dermascope, Dallas, Tex. 75202.

However, the use of glycolic acid, as noted in these patents, has been criticized in U.S. Pat. No. 4,294,852 of Wildnauer, which alleges that the use of certain alcohols in combination with alpha-hydroxy acids permits their use in significantly lower concentration to achieve the same result.

However, Wildnauer '852 teaches the use of alpha-hydroxy acids in a composition with an aqueous phase containing water or in a lipid.

What Wildnauer does not teach is the use of an alpha-hydroxy acid, such as glycolic acid, and a solvent such as acetone impregnated into a pad, such as a medicated cleansing pad or a cosmetic applicator pad.

Cosmetic applicator pads and/or medicated cleansing pads have been described in use with salicylic acid and alcohol, as noted in U.S. Pat. No. 4,891,228 of Thaman. Other patents relating to cosmetic or medicated applicator pads include U.S. Pat. No. 3,706,595 and RE 28,957 of Drelich; U.S. Pat. No. 3,778,341 of Plumnner; U.S. Pat. No. 4,341,213 of Cohen; U.S. Pat. No. 4,719,226 of Otsuka and U.S. Pat. No. 4,738,848 of Yoshida. Moreover, U.S. Pat. No. 4,514,385 of Damani makes use of salicylic acid in an anti-acne aqueous gel delivered in a polymer vehicle.

However, alpha hydroxy acids, such as glycolic acid are much better at treating skin conditions, because of their activity in relation to the removal of dead skin layers and moisturizing and treating live skin. Moreover, glycolic acid is the preferred alpha hydroxy acid because it penetrates the dermal layers better by virtue of its relatively smaller molecular size than other alpha hydroxy acids having larger molecular sizes, such as lactic acid. Furthermore, glycolic acid acts better at peeling and/or exfoliating skin when used synergistically in combination with relatively low concentrations of acetone.

U.S. Pat. No. 4,608,370 of Aronsohn for a skin formulation discloses the use of lactic acid, salicylic acid, alcohol and resorcinol administered once in a single application, where the intended effect is expected to occur over a week's period for removal of dead skin in what is referred to as "peeling" in a non-irritating manner.

U.S. Pat. No. 4,830,854 to Copelan teaches use of salicylic acid in a pad for desqualmation of skin, epidermal hydration, along with diffuse loosening of a foreign body embedded in the skin.

U.S. Pat. No. 5,164,413 to Willis teaches treatment of acne with controlled irritation so that blemished skin dies after minor irritation and is replaced by healthy, fresh skin in the process known as exfoliation. To accomplish this Willis teaches that earlier prior art prior used such formulations which contained resorcinol, lactic acid, salicylic acid and ethanol to produce a "glowing" of acne afflicted skin followed by peeling of the dried dead skin layer and the growth of fresh new skin.

Other related preparations for skin treatment include U.S. Pat. No. 4,035,513 of Kumano, U.S. Pat. No. 4,124,720 of Wenmaekers, U.S. Pat. No. 4,195,077 of Marsh, U.S. Pat. No. 4,287,214 of Van Scott, U.S. Pat. No. 4,505,925 of Elslager, and Yu, U.S. Pat. No. 4,695,452 of Gannis, U.S. Pat. No. 4,824,865 of Bowser, U.S. Pat. No. 4,931,591 of Buhlmayer and U.S. Pat. No. 5,110,603 of Rau.

Products on the market are derivatives of the aforementioned patents. For instance, among the examples of published prior art, there exists an advertisement for "Fresh and New"™ of *The Vitamin Shoppe®*, a manufacturing and retail establishment located in New York, N.Y. The advertisement discloses a single use product including an alpha hydroxy acid, namely lactic acid with vitamins, which is used in low concentrations in topical applications for treating acne, age spots and irregular skin pigmentation. This is similar to U.S. Pat. No. 5,153,230 of Jaffrey, which discloses an alpha hydroxy acid, such as glycolic acid, with vitamins. The present invention uses a combination of skin treatment materials and methods and is a kit. This is greatly different from "Fresh & New"™.

Additionally, the "Fresh & New"™ advertisement discloses that lower concentrations of alpha hydroxy acids in topically applied products may have a beneficial effect when used over time. The present invention uses reduced concentrations of the alpha hydroxy acids glycolic acid and lactic acids, but does so in a unique synergistic combination with acetone and salicylic acid in a pad with standardized unit doses, where the acetone acts as both a solvent and a peeling agent and the alpha hydroxy acids act both as peeling agents and moisturizers.

In another advertisement for "Herbal Citrus Fruit Exfoliant"™ of Paul Penders, Petaluma, Calif., it is taught that alpha hydroxy acids are good skin exfoliants, which is similar to the aforementioned patents of Van Scott and Yu. The present invention makes use of glycolic and lactic acids in a unique synergistic combination with acetone and salicylic acid. This method of use as a peel and a kit further are different.

In yet another advertisement entitled "Beauty News", Edition 17, 1993, of Reviva Labs, Haddonfield, N.J., there is discussed at pages 2, 6 and 22 a once-per-week home skin peel material in a cream base wherein salicylic acid is the primary exfoliant. On page 7 of the Reviva Labs advertisement brochure there is disclosed that this Reviva Labs salicylic acid skin peel is gentler than glycolic acid because it claims that glycolic acid irritates the skin and causes a stinging sensation. This unpatented reference relies upon salicylic acid, as taught in U.S. Pat. No. 4,830,854 of Copelan and U.S. Pat. No. 4,891,228 of Thaman. Moreover, the Reviva products so not use acetone as both a degreaser and a peeling agent, and the Reviva products are not provided in a kit with standardized dosages in applicator pads of prescribed abrasiveness.

In contrast, the present invention utilizes glycolic acid and produces almost no stinging sensation when applied to intact skin, and the Reviva Labs advertising disclosure thus teaches away from the present invention. Unlike the Reviva Labs salicylic acid skin peel, the present invention is applied by a user at least once per day, not once per week as in the aforementioned advertisement. In addition, the present invention has a unique and synergistic combination of peeling agents including acetone, which is absent in the advertisement of Reviva Labs at pages 2, 6 and 22.

On pages 9, 15 and 22 of the Reviva Labs advertising brochure, there is disclosed a skin peeling composition utilizing glycolic acid which has been polymerized. In contrast, the present invention needs no such polymerization of an active skin peeling agent, since it employs a unique synergistic combination of low unit doses of peeling agents.

At page 18 of the Reviva Labs advertising brochure, there is disclosed a plurality of step-wise programs for the respective treatments of varying skin conditions. They do not use a peeling method. However, unlike the present invention, the Reviva Labs advertisement does not teach standardization of doses of peeling materials nor is there disclosure of the unique and synergistic combination of peeling ingredients provided by the present invention.

At page 23 of the Reviva Labs advertisement, there is disclosed trial kits of various skin condition treatment products. However these kits are merely small trial size containers of various skin condition treatment products. Unlike the present invention, however, these materials do not contain the unique and synergistic combination of peeling agents of the present invention, nor are there application pads of selected abrasiveness provided therewith, nor is there a method or object to peel.

In connection with topical use of acetone, the following prior art is relevant: U.S. Pat. No. 5,133,967 to Smith for a skin toning composition which proposes the use of glycol ether instead of acetone and alcohol to degrease and de-fat the skin. U.S. Pat. No. 5,154,174 describes the use of acetone as a skin drying agent in preparation for attachment of transdermal electrodes to the skin. U.S. Pat. Nos. 5,145,858 and 5,140,047, 5,134,150 and 4,847,270 for bactericides teach acetone for drying the skin, in conjunction with moisturizers, such as glycerol or castor oil. U.S. Pat. No. 5,091,379 describes acetone in an anti-inflammatory composition. U.S. Pat. Nos. 5,049,381 and 4,980,378 disclose the use of acetone for penetration of skin tanning coloration compositions or products. Other U.S. patents describing the drying effects of acetone include U.S. Pat. Nos. 4,963,557, 4,883,669 4,877,805, 4,847,270 4,844,098, 4,837,378, 4,735,798 and 4,603,146. Moreover, the New Jersey Department of Health "Hazardous Substances Fact Sheet: Acetone" Cas. No. 67-64-1, DOT No. UN 1090, Feb. 1989 warns that excessive use of acetone causes skin dryness.

However, none of these prior art documents teach the use of acetone as a peeling agent, as opposed to a drying agent.

However, such use can be supported, since in high concentrations acetone has been shown to cause blistering or excessive peeling by abnormal erosion of skin layers, as noted in Kechijian, "Nail Polish Removers: Are They Harmful?", Dept. of Dermatology, N.Y.U. School of Medicine, New York, N.Y., published by W. B. Saunders Company, 1991.

In the prior art, chemical peeling has been done in dermatologists' aestheticians' and cosmetologists' offices, and has been accomplished over a period of minutes or hours, generally in a single visit. The problems with such chemical peels include use of relatively high concentrations of such peeling agents as glycolic acid, trichloroacetic acid and phenol compounded into a suitable vehicle, with concentrations being typically from 30% up to as much as 90% in the prior art. Traditional chemical peeling, then, has been swift, harsh, often painful, and, due to the harshness has been undesirable.

In the course of chemical peeling surface debris, including dead skin cells, are removed partly through mechanical abrasive action of applying and removing the chemical peel agents and partly through the activity of the chemical peeling agents which, among other effects, break bonds by which dead skin cells adhere to each other and adhere to living skin cells. In the prior art, peeling agents have been applied and then neutralized and/or physically removed from the skin after the desired treatment time period has elapsed.

In the past, where the peeling agents have not been removed or neutralized, and the peeling compositions have been left on the skin under the direction of a physician, the effect of a relatively long duration of skin contact with the peeling compositions has been wounding and irritation of the skin due to the high concentrations of the peeling agents.

Chemical peeling can be done in varying degrees of depth, typically called light, superficial, medium, and deep peels. A light or superficial peel is generally one which is comparatively superficial in effect and medium or deep chemical peels are ones in which peeling agents are used to produce a moderate to severe wound to the skin. However, a deep peel achieves a much more profound effect, and does so quickly, in minutes or hours. As a result, pain and inflammation usually result. Deep peeling usually produces redness lasting several days, a large and deep separation of dead skin, and the exposure of what, before the deep peel, was relatively deep living skin tissue.

The results of medium and deep peeling are not equivalent to the results of light or superficial peels or exfoliation. Whereas medium and deep peeling potentially produces undesirable redness, itching, pain, inflammation and unwanted or excessive peeling of living tissue, which may last days after the deep peel treatment, light or superficial peels produce few or no such undesirable side effects.

The cosmetic results of medium and deep peeling are more dramatic and more visible than the results available with light or superficial peeling and exfoliation. But where excessive or prolonged and unwanted peeling occurs in the aftermath of a medium or deep peel treatment, it is difficult or impossible to apply cosmetics to the affected skin due to the continued peeling and due to the pain, itching, inflammation and redness of the skin.

However, it should be noted that prior art medium and deep peeling and exfoliation is accomplished by the application of high-concentration peeling agents either in a single treatment session, or, at most, over a period of repetitive treatments over several days in a professional setting, i.e., the office of a dermatologist, an aesthetician or a cosmetologist.

In addition, the prior art does not provide for standardization of peeling or exfoliation. For example, a professional practitioner, i.e., a dermatologist, aesthetician or cosmetologist applies skin peeling agents which the practitioner has purchased containing individual ingredients such as glycolic acid. Prior art practitioners have used a variety of application methods, with no standardized quantity of agents being applied. Therefore there is no standardization of any part of the chemical peeling process in any of the prior art. By so doing, there can be no standardization of peeling materials or their concentrations among skin treatment practitioners.

In addition to the widely variable ingredients and concentrations of skin peel agents, there has been no standardization in the preparation of skin before application of the peeling agents, no standardization of the duration of skin contact with the peeling agents, no standardization of the degree of abrasiveness employed in the course of treatment, and no standardization of post-treatment for affected skin. The aforementioned lack of standardization has produced unpredictable results in the art of skin peeling/exfoliation.

As a general matter, skin to be peeled has been first cleansed in the prior art. In some prior art, there has also been another intermediate preparatory step in which various agents are applied to the skin in order to more effectively degrease it. After the skin is prepared by cleansing and/or degreasing, the peeling agents have been applied in the prior art. The peeling agents are then neutralized and/or removed after a non-standardized duration. Finally, affected skin has been topically treated with a moisturizer or other after-care preparation.

Additional disadvantages of the prior art have been the nonstandardization in the additional critical areas of variability in the effectiveness and depth of skin penetration achieved by the skin peeling agents, due to uncontrolled variability in preparatory degreasing; variability in types and concentrations of peeling agents due to the presence or absence of solvents such as alcohol mixed with and applied with the peeling agents themselves; variability in the duration of peeling agent contact with the skin; variability in degree of abrasiveness employed in the course of skin peeling or exfoliation; and, variability in the materials, manner and frequency of post-peel skin treatment. There is also no way for a professional to know how much of the peeling agent to apply as the dose has not been premeasured or standardized.

OBJECTS OF THE INVENTION

It is an object of the present invention to provide a skin peeling/exfoliating system for at-home use.

It is an object of the present invention to provide a skin peeling/exfoliating system which eliminates the necessity and avoids the need for expensive inconvenient professional supervision for peeling or exfoliation skin treatment.

It is an object of the present invention to provide a skin peeling/exfoliating system which provides for low concentrations of peeling/exfoliating agents.

It is an object of the present invention to provide a skin peeling/exfoliating system which provides for repeated gentle application of peeling/exfoliating agents over a selected period of days.

It is an object of the present invention to provide a skin peeling/exfoliating system which provides for standardization in the nature, dosage and concentration of peeling/exfoliating agents.

It is an object of the present invention to provide a skin peeling/exfoliating system which provides for standardization in the preparation of the skin before and after the application of peeling/exfoliating agents.

It is an object of the present invention to provide a skin peeling/exfoliating system which provides results for the user which are desirable, predictable and reliable.

It is an object of the present invention to provide a skin peeling/exfoliating system which eliminates redness, pain, itching, unwanted or excessively deep peeling associated with the prior art.

It is an object of the present invention to provide a skin peeling/exfoliating system which provides for convenient application of the aforedescribed standardized skin peeling/exfoliating system.

It is an object of the present invention to provide a skin peeling/exfoliating system which provides a kit for convenient application of the present invention.

It is an object of the present invention to provide a skin peeling/exfoliating system which provides for a skin peeling/exfoliating agent which comprises a unique combination of skin peeling/exfoliating materials.

It is an object of the present invention to provide a skin peeling/exfoliating system which provides a delivery system using cosmetic applicator pads and/or medicated applicator pads having a selected degree of abrasiveness.

It is an object of the present invention to provide a skin peeling/exfoliating system which provides a delivery system using cosmetic applicator pads and/or medicated applicator pads which are saturated with a measured quantity of a selected material.

It is an object of the present invention to provide a skin peeling/exfoliating system which provides a plurality of applicator pads saturated with materials for a first cleansing step.

It is an object of the present invention to provide a skin peeling/exfoliating system which provides a plurality of applicator pads saturated with materials for a second degreasing step.

It is an object of the present invention to provide a skin peeling/exfoliating system which provides a plurality of applicator pads saturated with materials for a third peeling/exfoliating step which is also a moisturizing step.

It is an object of the present invention to provide a skin peeling/exfoliating system which provides a fourth moisturizing and/or soothing step employing a suitable anti-inflammatory material.

It is an object of the present invention to provide a skin peeling/exfoliating system which provides a therapeutic phase followed by a maintenance phase.

It is an object of the present invention to provide a skin peeling/exfoliating system which provides a method of treating and improving the appearance of aging skin.

It is an object of the present invention to provide a skin peeling/exfoliating system which provides a method of treating and improving the appearance of skin with hyperpigmentation.

It is an object of the present invention to provide a skin peeling/exfoliating system which provides a method of treating and improving the appearance of acne.

It is an object of the present invention to provide a skin peeling/exfoliating system which provides a method of treating and improving the appearance of sensitive skin.

It is an object of the present invention to provide a skin peeling/exfoliating system which provides a method of treating and improving the appearance of composite dry-oily skin.

It is an object of the present invention to provide a skin peeling/exfoliating system which provides an anti-inflammatory ingredient to reduce inflammation and to increase user comfort.

It is an object of the present invention to provide a skin peeling/exfoliating system which provides a single agent which is left on the skin, and which, by the virtue of leaving it on, becomes both a skin moisturizer and a treatment for aging skin, photo-aging skin, dry skin, sensitive skin, thin skin, eczema, acne, hyperpigmented skin, and composite skin.

It is an object of the present invention to use acetone as a skin peeling agent.

It is an object of the present invention to use and to take advantage of the additive effect of the use of acetone as a skin peeling agent when applied (1) as a degreaser, and additively, when additionally applied (2) as a component of a synergistic combination of low-concentration mild peeling agents.

It is an object of the present invention to use acetone as a component of a synergistic combination of skin peeling agents.

SUMMARY OF THE INVENTION

In addressing the problems of disadvantageous variability found in the prior art, the present invention provides a composition, a method, and a kit for at-home chemical skin peeling which is gentle in that the concentrations of the active skin peeling ingredients is far lower than that available in dermatologists' offices. The composition of the present invention provides a medically effective composition and method in that the low concentrations of peeling agents permit those peeling agents to be left on the skin of the user for a relatively extensive duration.

Such long-duration skin contact with the peeling agents accomplishes the slow peeling effects which are an object of the present invention. In addition, the medical efficacy of the present invention in not irritating or wounding the skin in a manner perceptible to the user is a further novel advantage.

Because the peeling composition of the present invention is of low concentration and is thus medically effective in preventing skin wounding which is perceptible, the composition of the present invention may be, and is intended to be left upon the skin of the user without the neutralization or removal required in the prior art. Thus, the present invention is designed to be used daily over a period of weeks to produce the same or a superior result compared to light or superficial chemical peels alone.

The present invention is better than a glycolic acid cream because the acetone in the present invention strips the skin of oil and grease and thus allows the peeling agents to penetrate deeper. The peeling agent in a cream base cannot penetrate as deeply. Thus with the acetone component of the present invention the peeling agents penetrate deeper and are more effective in peeling the skin.

Moreover, acetone itself acts as a peeling agent, which acts synergistically with other peeling agents, such as alpha hydroxy acids, preferably glycolic acid.

The key novel aspects is the present invention's ability to deliver the peeling agents to the appropriate layers of skin where peeling is to occur.

In addition, the present invention standardizes the materials used as skin exfoliating agents; standardizes the concentration and the dosage of said materials by providing a unit dosage; standardizes the cleansing and degreasing phases of skin treatment; standardizes the depth of penetration and activity of the peeling agents; standardizes the post-peel treatment of the affected skin; eliminates the need to neutralize or remove the peeling agents and thereby eliminates the need to standardize the duration of skin contact with the peeling agents; and standardizes the number of treatment repetitions and the interval between repetitions for the treatment of skin according to the present invention.

In addition, the present invention provides standardization in the critical areas of peeling agents and their respective concentrations, standardization in preparation of skin before application of the peeling agents, eliminates the need for standardization of the duration of skin contact with the peeling agents, standardization of the degree of abrasiveness employed in the course of skin preparation and treatment, and standardization of treatment moisturizing for affected skin and is thus a major step forward in the art of skin peeling and exfoliation.

In contrast to the prior art which requires expensive and potentially inconvenient professional treatment for skin peeling and exfoliation, the present invention provides convenient and inexpensive skin peeling/exfoliating at home, in a non-professional setting, utilizing low concentrations of peeling agents applied only once per day over a period lasting a minimum of five days. Other differences between the present invention and the prior art will be fully set forth herein.

In addressing the aforementioned objects, the present invention provides a composition, a method, and a kit for at-home chemical skin peeling which is gentle in that the concentrations of the active skin peeling ingredients is far lower than that utilized in dermatologists' and aestheticians' offices. The composition of the present invention is designed to be used daily over a period of weeks to produce the same or a superior result compared to chemical peels available in an intense, harsh dermatological treatment lasting merely for a period of minutes or hours.

One of the most important novel features of the present invention derives from the fact that its concentrations of skin peeling agents is drastically reduced compared to typical prior art compositions. As a consequence, the present invention produces the desired skin peeling effects in a series of painless treatments.

Prior art professional skin peeling not done in the home has generally comprised the following sequence of steps (1) cleansing the skin; (2) application of a degreaser; (3) application of active skin peeling materials; and (4) neutralizing or removal of the active skin peeling materials.

The present invention utilizes the first three steps, but does not need to remove or neutralize the active skin peeling materials because the reduced concentrations thereof can be left upon the skin. Thus, the present invention has novel and very significant modifications of prior art skin peeling. In addition, the present invention uses a fifth and in some cases a sixth step in variously addressing some of the respective skin conditions.

The novel modifications of the present invention which distinguish over the prior art occur as follows: (a) in the degreasing step, which is generally step 2, by using (i) acetone in a home-use skin preparation material and (ii) by providing selectability of the level of applicator pad abrasiveness; and (b) in the peeling/exfoliating step, which is generally step 3 of the present invention, by including in the peeling/exfoliating combination of (i) the use of acetone as both a skin penetrating agent and a peeling agent, and (ii) the combination of a peeling agent composition preferably including acetone, glycolic acid and lactic acid with a moisturizing material, which material is applied to the skin to accomplish both gradual peeling and moisturizing at the same time.

Although acetone is a peeling agent as set forth earlier, moisturization is accomplished because glycolic acid and lactic acid act not only as peeling/exfoliating agents, but are humectants as well. When left on the skin, glycolic acid and lactic acid also act as moisturizers. They can be left on the skin in the present invention because they are in low concentrations.

The embodiments of the present invention vary somewhat as each specific type of skin condition is addressed, i.e., aging skin, dry skin, photo aged skin, hyperpigmentation, darkly pigmented skin, acne, eczema, thin skin, sensitive skin and composite dry-oily skin.

In addition to the foregoing aspects of novelty, the present invention requires that the aforementioned conventional four steps be accomplished in a novel manner. The present invention provides that the four steps be performed by applying the given material by means of a cosmetic applicator pad pre-saturated with a unit dose of the given material for the respective cleansing, degreasing and peeling/exfoliating steps, which are generally steps 1–3 in the present invention. In addition, the cosmetic applicator pads of the present invention are further selected to provide a desired level of abrasive efficiency selected from the categories mild, moderate and strongly abrasive. The prior art does not teach the use of cosmetic applicator pads with specific and selected abrasive capabilities, as does the present invention.

Variation in applicator pad abrasiveness is achieved by selecting suitable materials for pad construction, such as cotton, nylon, polyester, styrene and the like, singly or in combination. The pad may have an applicator surface which is of fibrous consistency or otherwise suitably textured with a blend of semi-rigid and soft materials for producing an abrasive effect for scraping, removing and cleansing action.

The penetration depth and effectiveness of the peeling agents, such as acetone and the alpha hydroxy acids such as glycolic acid and lactic acid, are affected by pad abrasiveness because a given level of pad abrasive capability results in and/or controls the degree of mechanical exfoliation of dead skin, thus exposing underlying living skin tissue more effectively. By taking off the top layers of dead skin, the skin degreaser is allowed to work more effectively, providing a corresponding level of skin degreasing efficiency when the skin is wiped with the pad during the cleansing and/or degreasing steps of treatment. Pad abrasive efficiency thus controls the amount of natural oil and grease left upon skin which has been prepared for topical application of the peeling agent. The greater the abrasive efficiency of the pad used for cleansing and/or degreasing the skin, the deeper the peeling agent will penetrate, thereby providing enhanced peeling agent effectiveness.

The user of a pre-saturated cosmetic applicator pad for the pad-utilizing steps of the present invention treatment process gains the convenience of being apply to accurately apply a unit dose, i.e., a measured quantity, of each respective pad-applied materials. The unit dose of the degreaser and of the peeling/exfoliating agent composition may vary, but is preferably about 0.75 grams per presaturated applicator pad. Thus predictable and desirable results are provided by the present invention, in contrast to the prior art where arbitrarily selected doses of needed materials have not been as low as those used in the present invention.

The kit of the present invention provides convenient packaging and supplies a user with the respective cosmetic applicator pads for each of the three pad-utilizing steps, i.e., cleansing, degreasing, and peeling/exfoliating, in a quantity sufficient to provide treatment for a selected number of days, the user applying the treatment at a selected periodic interval, for example, once daily.

An additional novel feature of the present invention is that the peeling agent, once applied by the user, is left upon the skin for at least several hours. It is not neutralized nor is it removed because it is a moisturizer and because the concentration of peeling/exfoliating agents is low, giving the present invention a mild, gradual peeling/exfoliating effect.

The present invention can be left on the skin due its low concentration of gentle peeling agents. The present invention is intended to be used, preferably at night before retiring, and in the morning, variously, according to the type of skin condition addressed. The preferred treatments, and times of day preferred will be further set forth in detail. No matter what time of the day the peeling/exfoliating materials are applied, they are intended to be left in contact with the user's skin until, typically, washed off by normal bathing after a period of hours. In contrast, the prior art requires the application followed by the relatively quick neutralization or removal of peeling agents. This quick removal or neutralization is obviously necessary due to the high concentrations of peeling agents used in the prior art, with their attendant harshness and action deep within the skin and the wounding of living skin tissue.

An additional novel feature of the present invention is that skin treatment is provided in two general phases—a therapeutic phase and a maintenance phase. The therapeutic phase is conducted by applying a relatively higher concentration of the active peeling/exfoliating agent periodically at a selected interval, e.g., once daily, to produce the desired skin peeling/exfoliation over a period of days. In the preferred embodiment of the present invention the desired skin peeling is achieved over a seven day period, with alternate embodiment time periods employing varying numbers of days, e.g., 5 days, 14 days, or more than 14 days.

The difference in preferred 7-day therapeutic phase treatment and therapeutic phase treatments for other selected numbers of days may be achieved, as described in greater detail elsewhere, by varying (a) the abrasiveness of the applicator pads; (b) the nature and concentration of the degreaser, with the selected degreasing efficiency proportional to the concentration of acetone therein, and the degreaser efficiency being selected from among the categories of mild, moderate, and strong, as will be more fully set forth below; and (c) the concentrations of the peeling/exfoliating agents. The therapeutic phase application is typically done at a time when the user requires a relatively stronger treatment with the present invention, such as when beginning use of the invention for the first time.

In contrast to treatment during the therapeutic phase, the maintenance phase of the present invention comprises lower-concentration maintenance applications of the peeling/exfoliating agent of the present invention repeated at selected periodic intervals, e.g., twice daily, over a one-month period. The maintenance phase is intended to provide the user with a cosmetic result which prolongs and maintains the healthy and attractive appearance of the skin resulting from the therapeutic phase. The one-month maintenance period is intended to be extended for an indefinite number of months, with the user having the option to repeat the therapeutic phase as desired.

Selecting the rate of skin peeling/exfoliating during the therapeutic phase is accomplished by varying, singly or in combination (a) applicator pad abrasiveness; (b) degreaser composition; (c) peeling/exfoliating agent concentration; and (d) the number of treatments involving the aforementioned steps. It has been found that keeping the concentrations of the peeling agents constant, and varying the type and concentration of the degreasing agent critically produces a change in the peeling rate.

It is thought that this is so because a more effective degreaser, such as an acetone component in the degreaser, in relatively high concentration, will be relatively more effective in removing skin surface oil, thereby more effectively exposing underlying skin to contact with the peeling agents. Acetone has not been used in home skin treatment/peeling compositions in the prior art because it is far too harsh and produces far too much skin drying. Thus, the prior art has taught away from this critical novel feature of the present invention.

Upon use of acetone in the degreasing step, and upon further use of an acetone component in the peeling agent composition, the peeling/exfoliating agent of the present invention penetrates the skin deeper and more effectively than if skin oils had been less efficiently removed. Also, substituting alcohol as an degreaser in place of all or a portion of acetone will affect, and thus control the rate of peeling, since alcohol is a less efficient solvent for skin oil than is acetone. The degreaser of the present invention, as elsewhere set forth, is typically a mixture of alcohol, acetone and water. The concentrations of the degreaser components can thus be varied to produce a desired rate of skin peeling.

The third manner in which the rate of skin peeling may be controlled is by selecting a cosmetic applicator pad of suitable abrasiveness, as has been more fully set forth above.

The present invention provides respective kit assemblies for treating the respective skin conditions set forth above. Each respective kit assembly includes an effective and convenient instructional means, such as an instructional pamphlet or a videotape or other instructional means containing thereon indicia for administration of sequentially applied components according to steps needed for the respective skin condition to be treated.

The kit assembly also provides a sequential dispenser means containing a plurality of daily sets of kit sub-assembly components, such as a series of jars containing a supply of presaturated applicator pads having, respectively, cleanser, degreaser and peeling agent therein. In addition, kits are provided with containers such as bottles or tubes of other non-pad-requiring ingredients for the respective skin conditions, such non-pad-requiring materials being, for example, a moisturizer, a sun screen, etc as more fully set forth below. In addition to respective kits being specific for treatment of each aforementioned skin condition, kits are further respectively specific with regard to whether a given kit is to be used for the therapeutic phase or, in the alternative, for the maintenance phase.

Generally, and except as set forth for specific skin conditions in more detail below, each kit provided in the present invention has sub-assembly components including therein the following:

a. a step 1 container including a supply of applicator pads saturated with a premeasured quantity of a non-soaping non-detergent cleanser lotion; the supply includes two such pads for each day of intended use, one for a morning use and one for an evening use e.g., 14 step-1 pads for 7 days of intended use, for example, in the therapeutic phase.

Since the maintenance phase is intended to be used following the preferably 7-day therapeutic phase, and to provide daily maintenance treatments for one month, the corresponding maintenance kit would preferably contain 60 step-1 cleansing pads for 30 days of intended twice-daily maintenance treatments. The remaining saturated pad descriptions below are similarly intended to be understood to apply, respectively to a preferably therapeutic phase of 7 days and a preferably maintenance phase of 30 days.

b. a step-2 container including a supply of applicator pads saturated with a premeasured quantity of degreaser.
c. a step-3 container including a supply of applicator pads saturated with a premeasured quantity of peeling/exfoliating agent.
d. a step-4 container such as a tube or bottle containing a post-treatment moisturizing and anti-inflammatory material.
e. a step-5 container such as a tube or bottle containing a moisturizing sun screen material.
f. for certain skin conditions, a suitable step 6 container such as a tube or bottle with a required material, as detailed below.

Each day of the course of treatment, one component of the kit assembly is used for both applying and removing the agents in a non-professional setting according to the aforementioned steps, which are performed at selected periodic intervals, e.g., once daily by the user as directed by the instructions for the particular kit for the particular respective skin condition for the particular respective number of days of that kit's embodiment [e.g., 7-day therapy phase treatment kit for aging skin]. The step-wise procedure employed by the user is generally described in further detail as follows:

a. step 1—cleansing the skin to be treated with a non-soaping non-detergent cleanser lotion applied with an applicator pad having a preselected level of abrasiveness, said pad being wiped across the skin to be treated with mild manual pressure;
b. step 2—applying a suitable degreasing agent to degrease the skin to be treated, the degreasing agent being applied with an applicator pad having a preselected level of abrasiveness and the pad being presaturated with a measured quantity of degreasing agent in the manner set forth in step "a";
c. step 3—applying to the skin to be treated a composition of mild skin peeling agents of a composition elsewhere described herein, with an applicator pad presaturated with a measured quantity of said skin peeling agents in the manner set forth in step "a", the user exercising care in the application of moderate manual pressure to the applicator pad as it passes over the skin to be treated so as to provide a mild abrading of said skin; and
d. step 4—applying a suitable moisturizing anti-inflammatory cream to the skin to be treated.
e. step 5—applying a special sun screen.

The present invention provides three types of moisturizing sun screens.

Type 1—employs a hydro-alcoholic gel for acne patients, because this is a drying-type sun screen.

Type 2—employs a rich moisturizing sun screen for the photo aging skin and aging skin.

Type 3—employs a bleaching agent—hydroquinone—for hyperpigmented and darkly pigmented skin.

Skin bleaching is separately provided by the present invention as a separate step for the pigmented skin, i.e., hyperpigmented skin and darkly pigmented skin. Bleaching would be done by applying a hydroquinone bleach-containing material in the evening. The hydroquinone bleach, as described in more detail below, is applied after the peeling agent has been applied and before the moisturizer is applied. Thus, the peeling/exfoliating agent, the hydroquinone bleach, and the moisturizer are all left on the skin to be treated all night long.

The present invention provides two types of anti-inflammatory moisturizer materials. Both have hydrocortisone in them.

Type 1—anhydrous preparation employed for aging skin.
Type 2—hydrous preparation used for all other skin types.

The skin peeling/exfoliating agents provided in step 3 of the present invention include low concentrations of, preferably, acetone, glycolic acid, salicylic acid, and lactic acid according to the Tables set forth below. In an alternate embodiment, a low-concentration quantity of resorcinol is provided as a peeling/exfoliating agent in combination with the aforementioned preferable peeling agents. The preferred embodiment of the composition of the peeling/exfoliating agent of the present invention is presented in Table 1 below, and the alternate embodiment composition containing resorcinol is presented in Table 2 below. Tables 1.1 and 2.1, respectively, set forth ranges and preferable concentrations for the therapeutic phase of the present invention, namely the 15-2-2 peeling/exfoliating composition. 15-2-2 refers to preferably 15% glycolic acid, 2% lactic acid and 2% salicylic acid. The Maintenance phase preferably utilizes 5-2-2, i.e., one-third the concentrations of the aforementioned peeling/exfoliating agents. The compositions and concentrations of the maintenance phase peeling/exfoliating agents are not here set forth because they are the same as those set forth in Tables 1, 1.1, 2, and 2.1, except that, instead of the 15-2-2 composition, the maintenance phase uses a 5-2-2 composition.

TABLE 1

Composition of Peeling/ exfoliating Agents
of the preferred Embodiment of the Therapeutic Phase
of the Present Invention
Materials are listed by Weight Percentages

| Material | From About | To About |
|---|---|---|
| Disodium EDTA | 0.01% | 0.3% |
| Sodium Benzoate | 0.01% | 1.0% |
| Witch Hazel E02 | 0.01% | 20% |
| Polysorbate-20 | 0.01% | 25% |
| Salicylic Acid USP | 0.1% | 5% |
| Lactic Acid USP | 0.1% | 20% |
| Glycolic Acid | 0.1% | 20% |
| Ammonia, dissolved | 0.1% | 35% |
| Germall 115 | 0.01% | 1.0% |
| Acetone | 0.1% | 10% |
| Alcohol | 1.0% | 50% |
| Purified Water Balance of composition | 100.0% | |

TABLE 1.1

Composition of Peeling/ exfoliating Agents
of the Preferred Embodiment of the Therapeutic Phase
of the Present Invention
Same as Table 1
Showing Preferred Concentrations
Materials are listed by Weight Percentages

| Material | Preferably About |
|---|---|
| Disodium EDTA | 0.1% |
| Sodium Benzoate | 0.2% |
| Witch Hazel E02 | 2.5% |

TABLE 1.1-continued

Composition of Peeling/ exfoliating Agents
of the Preferred Embodiment of the Therapeutic Phase
of the Present Invention
Same as Table 1
Showing Preferred Concentrations
Materials are listed by Weight Percentages

| Material | Preferably About |
|---|---|
| Polysorbate-20 | 1.0% |
| Salicylic Acid USP | 2.0% |
| Lactic Acid USP | 2.0% |
| Glycolic Acid | 15.0% |
| Ammonia, dissolved | 6.0% |
| Germall 115 | 0.2% |
| Acetone | 5.0% |
| Alcohol | 5.0% |
| Purified Water Balance of Composition to 100% | |

TABLE 2

Composition of Peeling/ exfoliating Agents of an
Alternate Embodiment of the Therapeutic Phase
of the Present Invention
With Resorcinol
Materials are listed by Weight Percentages

| Material | From About | To About |
|---|---|---|
| Disodium EDTA | 0.01% | 0.3% |
| Sodium Benzoate | 0.01% | 1.0% |
| Witch Hazel E02 | 0.01% | 20% |
| Polysorbate-20 | 0.01% | 25% |
| Salicylic Acid USP | 0.1% | 5% |
| Lactic Acid USP | 0.1% | 20% |
| Glycolic Acid | 0.1% | 20% |
| Resorcinol | 0.1% | 10% |
| Ammonia, dissolved | 0.1% | 35% |
| Germall 115 | 0.01% | 1.0% |
| Acetone | 0.1% | 10% |
| Alcohol | 1.0% | 50% |
| Purified Water Balance of Composition | 100.0% | |

TABLE 2.1

Composition of Peeling/ exfoliating Agents of an
Alternate Embodiment of the Therapeutic Phase
of the Present Invention With Resorcinol
Same As Table 2, Showing Preferred Concentrations
Materials are listed by Weight Percentages

| Material | Preferably About |
|---|---|
| Disodium EDTA | 0.1% |
| Sodium Benzoate | 0.2% |
| Witch Hazel E02 | 2.5% |
| Polysorbate-20 | 1.0% |
| Salicylic Acid USP | 2.0% |
| Lactic Acid USP | 2.0% |
| Glycolic Acid | 15.0% |
| Resorcinol | 2.0% |
| Ammonia, dissolved | 6.0% |
| Germall 115 | 0.2% |
| Acetone | 5.0% |
| Alcohol | 5.0% |
| Purified Water Balance to | 100.0% |

TABLE 3

Composition of Degreaser Composition
of the Present Invention
Materials are listed by Weight Percentages

| Material | From About | To About |
|---|---|---|
| Witch Hazel | 0.10% | 25% |
| Propylene Glycol | 0.10% | 25% |
| Camphor | 0.01% | 5% |
| Acetone | 0.1% | 10% |
| Alcohol | 1.0% | 80% |
| Sodium Borate | Trace | 1% |
| Purified Water Balance of Composition | 100.0% | |

TABLE 3.1

Composition of Step 2 - Degreaser Composition
of the Present Invention
Same As Table 3
Showing Preferred Concentrations
Materials are listed by Weight Percentages

| Material | Preferably About |
|---|---|
| Witch Hazel | 2.5% |
| Propylene Glycol | 3.0% |
| Camphor | 0.1% |
| Acetone | 5.0% |
| Alcohol | 51% |
| Sodium Borate | 0.1% |
| Purified Water Balance to | 100.0% |

The following specific compositions are provided for treatment of the respective skin conditions, as noted in Table 4 below. The quantities listed in Table 4 are total quantities, which will be divided uniformly into the number of pre-saturated applicator pads. For example, in the therapy phase of acne treatment, step 1 cleanser is listed as provided in saturated pads in a 2 ounce quantity. In like manner, all other listed component quantities are similarly divided evenly into subquantities for pad saturation for the relevant number of days.

It should be noted that, for the treatment of hyperpigmented skin and darkly pigmented skin, there are 6 steps provided, the sixth step being application of a sun screen in the morning and the fifth step being application of a moisturizer and anti-inflammatory combination in the evening. The active anti-inflammatory ingredient of the present invention is hydrocortisone. As set forth above, the individual treatments of the respective skin conditions in some cases require more than four steps. In addition, there is a separate morning and evening treatment for each respective skin condition. The individual skin conditions are treated generally as follows, and, more particularly, as set forth in summary form in Table 4 below.

Aging and Photo-Aging Skin—Therapy Phase

1. Cleansing twice daily is accomplished with a soap-free cleansing lotion designed to cleanse efficiently without excessive drying or irritation of the skin. A cleanser such as DEA lauryl sulfate in an emollient base and is used twice per day.

2. The degreaser is applied to deep clean the skin and remove excess sebum, which may reduce the effectiveness of the treatment pads. The degreaser is a hydro-alcoholic solution containing acetone in the concentration range of 0.1% to 10% but preferably 5% .

3. 15-2-2 Treatment Pads contain the peeling/exfoliating agent combination glycolic acid [preferably 15%, but over the possible range of 1–20%], salicylic acid [preferably 2%, but over the possible range of 0.1% to 5%], and lactic acid [preferable 2%, but over a possible range of 0.1% to 20%]. The 15-2-2 combination works synergistically with acetone as a peeling agent [preferably 5% but over the possible range of 0.1% to 10%]. The peeling/exfoliating agent combination is provided in a penetrating hydro-alcoholic vehicle containing acetone as a co-solvent to insure proper delivery of the peeling/exfoliating agent to the skin area to be treated. See Tables 1 and 2 for compositions and concentration ranges.

4. After the peeling/exfoliating treatment, the hydrocortisone balm for night-time use only is applied, containing the well-known anti-inflammatory and anti-pruritic drug hydrocortisone in the concentration range 0.1% to 2.5%, preferably 1%, in an anhydrous base.

5. A moisturizing sun screen is provided for morning application and day-time use to replenish moisture to the skin and maintain the moisture balance of the skin. The moisturizing sun screen is further provided with broad spectrum UV screens [i.e., screens for UVA and UVB] for protection from sunlight after therapy. The moisturizing sun screen contains octyl methoxycinnamate in the concentration range of 1.5%–7.5%, preferably 7.5% and benzophenone-3 in the range from 0.1% to 6%, preferably 4%.

Aging Skin and Photo-Aging - Maintenance Phase

1. Cleansing twice daily is accomplished with a soap-free cleansing lotion designed to cleanse efficiently without excessive drying or irritation of the skin. A cleanser such as DEA lauryl sulfate in an emollient base and is used twice per day.

2. The degreaser is applied twice daily to deep clean the skin and remove excess sebum, which may reduce the effectiveness of the treatment pads. The degreaser is a hydro-alcoholic solution containing acetone in the concentration range of 0.1% to 10% but preferably 5%.

3. Gentle twice daily peeling/exfoliation is accomplished by the use of the 5-2-2 treatment pad during the maintenance phase. The 5-2-2 pad contains glycolic acid [preferably 5%, but over a possible range of 1–20%], salicylic acid [preferably 2%, but over a possible range of 0.1% to 5%], and lactic acid [preferably 2%, but over a possible range of 0.1% to 20%]. The peeling/exfoliating agent combination is carried in a penetrating hydro-alcoholic vehicle containing acetone in the concentration range of 0.1% to 10% but preferably 5% as a co-solvent to insure proper delivery of the peeling/exfoliating agent to the skin area to be treated. See Tables 1 and 2 for compositions and concentration ranges.

4. After the peeling/exfoliating step, the hydrocortisone balm is applied at night time, containing the well-known anti-inflammatory and anti-pruritic drug hydrocortisone in the concentration range 0.1% to 2.5%, preferably 1% in a hydrous base.

5. A moisturizing sun screen is provided for morning application and day-time use to replenish moisture to the skin and maintain the moisture balance of the skin. The moisturizing sun screen is further provided with broad spectrum UV screens [i.e., screens for UVA and UVB] for protection from sunlight after therapy. The moisturizing sun screen contains octyl methoxycinnamate in the concentration range of 1.5%–7.5%, preferably 7.5% and benzophenone-3 in the range from 0.1% to 6%, preferably 4%.

Sensitive Skin, Therapy Phase

For sensitive skin, the therapy phase is comprised of the following steps:

1. Cleansing is accomplished with a soap-free cleansing lotion designed to cleanse efficiently without excessive drying or irritation of the skin. A cleanser such as DEA lauryl sulfate in an emollient base and is used twice per day.

2. The skin is degreased gently, without excessive abrasion or further use of detergents or solvents. The skin further cleansed using ultra pure rehydrated aloe vera juice and a blend of sodium PCA and other humectants, such as methyl glyceth-20 in a water-based vehicle.

3. 15-2-2 Treatment Pads contain the peeling/exfoliating agent combination glycolic acid [preferably 15%, but over the possible range of 1–20%], salicylic acid [preferably 2%, but over the possible range of 0.1% to 5%], and lactic acid [preferable 2%, but over a possible range of 0.1% to 20%]. The peeling/exfoliating agent combination is provided in a penetrating hydro-alcoholic vehicle containing acetone as a co-solvent to insure proper delivery of the peeling/exfoliating agent to the skin area to be treated. The 15-2-2 combination works synergistically with acetone as a peeling agent [preferably 5% but over the possible range of 0.1% to 10%]. See Tables 1 and 2 for compositions and ranges.

The penetrating effect refers to the ability of the vehicle to cause deep, even dispersion throughout the skin. A hydro-alcoholic vehicle is one containing both water and alcohol, comprising a two-solvent system.

4. The therapeutic balm, which is applied twice daily contains the well-known anti-inflammatory and anti-pruritic drug hydrocortisone in the range of 0.1% to 2.5% in a hydrous base. The therapeutic balm serves to promote hydration and reduce inflammation to increase user comfort, as may be needed with frequent treatment of sensitive skin.

5. Moisturization and Ultraviolet light [UV] protection is provided for morning and daytime use on sensitive skin by applying a quick absorbing oil free emulsion which is light in consistency and does not have a heavy or oily base. Broad spectrum [UVA and UVB] protection is provided without the use of oxybenzone, lanolins, glycols, etc. The UV filters are Octyl Methoxycinnamate in the range of 1.5% to 7.5% and Menthyl Anthranilate in the range of 1% to 10% and the oil-free emulsion itself is a water-based emulsion comprised of a water-based vehicle and an ester-based emollient phase.

Sensitive Skin, Maintenance Phase

For sensitive skin, the Maintenance phase is comprised of the following:

1. Soap-free cleansing twice daily is done during the maintenance phase. Cleansing is accomplished with a soap-free cleansing lotion as in the therapy phase, the cleanser being designed to cleanse efficiently without excessive drying or irritation of the skin.

2. The skin is degreased gently twice daily, without excessive abrasion or further use of detergents or solvents. The skin further cleansed using ultra pure rehydrated aloe vera juice and a blend of sodium PCA and other humectants, such as methyl glyceth-20 in a water-based vehicle.

3. Gentle twice daily peeling/exfoliation is accomplished by the use of the 5-2-2 treatment pad during the maintenance phase. The 5-2-2 pad contains glycolic acid [preferably 5%, but over a possible range of 1–20%], salicylic acid [preferably 2%, but over a possible range of 0.1% to 5%], and lactic acid [preferably 2%, but over a possible range of 0.1% to 20%]. The peeling/exfoliating agent combination is carried in a penetrating hydro-alcoholic vehicle containing acetone in the concentration range of 0.1% to 10% as a co-solvent to insure proper delivery of the peeling/exfoliating agent to the skin area to be treated. The 5-2-2 combination works synergistically with acetone as a peeling agent [preferably 5% but over the possible range of 0.1% to 10%]. See Tables 1 and 2 for compositions and concentration ranges.

4. After the peeling/exfoliating treatment, the therapeutic hydrocortisone balm is applied, containing the well-known anti-inflammatory and anti-pruritic drug hydrocortisone in the concentration range 0.1% to 2.5% but preferably 1%, in a hydrous base.

5. Sun protector is applied in the morning for day time use via quick absorbing, oil-free emulsion for sensitive skin. Broad spectrum [UVA and UVB] protection is provided without the use of oxybenzone, lanolins, glycols, etc. The UV filters are Octyl Methoxycinnamate in the range of 1.5% to 7.5% and Menthyl Anthranilate in the range of 1% to 10% and the oil-free emulsion itself is a water-based emulsion comprised of a water-based vehicle and an ester-based emollient phase.

Acne Treatment, Therapy Phase

1. Cleansing twice daily is accomplished with a soap-free cleansing lotion designed to cleanse efficiently without excessive drying or irritation of the skin. A cleanser such as DEA lauryl sulfate in an emollient base and is used twice per day.

2. The degreaser is applied to deep clean the skin and remove excess sebum, which may reduce the effectiveness of the treatment pads. The degreaser is a hydro-alcoholic solution containing acetone in the concentration range of 0.1% to 10% but preferably 5%.

3. 15-2-2 Treatment Pads contain the peeling/exfoliating agent combination glycolic acid [preferably 15%, but over the possible range of 1–20%], salicylic acid [preferably 2%, but over the possible range of 0.1% to 5%], and lactic acid [preferable 2%, but over a possible range of 0.1% to 20%]. The peeling/exfoliating agent combination is provided in a penetrating hydro-alcoholic vehicle containing acetone as a co-solvent to insure proper delivery of the peeling/exfoliating agent to the skin area to be treated. The 15-2-2 combination works synergistically with acetone as a peeling agent [preferably 5% but over the possible range of 0.1% to 10%]. See Tables 1 and 2 for compositions and concentration ranges.

4. A hydrocortisone moisturizer therapeutic balm is applied which is used at night time. This material uses the well-known anti-inflammatory hydrocortisone in a water-based emulsion.

5. A gel containing a topical acne preparation or group of preparations such as benzoyl peroxide is then applied in the morning, but not at night. Appropriate directions are provided in the kit of the present invention. The use of benzoyl peroxide to treat acne is well documented. This gel provides benzoyl peroxide U.S.P. in a non-irritating water based gel.

6. An acne treatment UV screen for morning application and daytime use is provided to reduce the user's UV exposure. The acne UV screen is a non-comedogenic, oil-free preparation containing octyl methoxycinnamate in the concentration range of 1.5%–7.5% , preferably 7.5%; homosalate 1–10%, preferably 5%; octyl salicylate 1.5–5%, preferably 5%; and benzophenone-3 in the range from 0.1% to 6%, preferably 4% to provide broad spectrum UVA and UVB protection in a hydro-alcoholic base. The user is instructed to use the acne UV screen liberally, i.e., to totally cover the area of therapy with the UV screen.

Acne Treatment Maintenance Phase

1. An antiseptic acne cleanser is provided which contains mild detergents to cleanse the skin and remove excess oil. The user is instructed to cleanse the skin at regular periodic intervals, preferably twice per day.

2. Gentle twice daily peeling/exfoliation is accomplished by the use of the 5-2-2 treatment pad during the maintenance phase. The 5-2-2 pad contains glycolic acid [preferably 5%, but over a possible range of 1–20%], salicylic acid [preferably 2%, but over a possible range of 0.1% to 5%], and lactic acid [preferably 2%, but over a possible range of 0.1% to 20%]. The peeling/exfoliating agent combination is carried in a penetrating hydro-alcoholic vehicle containing acetone in the concentration range of 0.1% to 10% as a co-solvent to insure proper delivery of the peeling/exfoliating agent to the skin area to be treated. The 5-2-2 combination works synergistically with acetone as a peeling agent [preferably 5% but over the possible range of 0.1% to 10%]. See Tables 1 and 2 for compositions and concentration ranges.

3. A gel containing a topical acne preparation or group of acne preparations, such as benzoyl peroxide is then applied twice daily in the morning, and at night, as per kit instructions.

4. An acne treatment UV screen for morning application and daytime use is provided to reduce the user's UV exposure. The acne UV screen is a non-comedogenic, oil-free preparation containing octyl methoxycinnamate in the concentration range of 1.5%–7.5% , preferably 7.5%; homosalate 1–10%, preferably 5%; octyl salicylate 1.5–5%, preferably 5%; and benzophenone-3 in the range from 0.1% to 6%, preferably 4% to provide broad spectrum UVA and UVB protection in a hydro-alcoholic base. The user is instructed to use the ache UV screen liberally, i.e., to totally cover the area of therapy with the UV screen.

5. Evening-use Hydrocortisone Moisturizer therapeutic balm—this material uses the well-known anti-inflammatory hydrocortisone in a water-based emulsion.

Hyper Pigmented Skin and Darkly Pigmented Skin—Therapy Phase

1. Cleansing twice daily is provided by the soap-free cleanser during the maintenance phase. Cleansing is accomplished with a soap-free cleansing lotion as in the therapy phase, the cleanser being designed to cleanse efficiently without excessive drying or irritation of the skin.

2. The degreaser is applied to deep clean the skin and remove excess sebum, which may reduce the effectiveness of the treatment pads. The degreaser is a hydro-alcoholic solution containing acetone in the concentration range of 0.1% to 10% but preferably 5%.

3. 15-2-2 Treatment Pads contain the peeling/exfoliating agent combination glycolic acid [preferably 15%, but over the possible range of 1–20%], salicylic acid [preferably 2%, but over the possible range of 0.1% to 5%], and lactic acid [preferable 2%, but over a possible range of 0.1% to 20%]. The peeling/exfoliating agent combination is provided in a penetrating hydro-alcoholic vehicle containing acetone as a co-solvent to insure proper delivery of the peeling/exfoliating agent to the skin area to be treated. The 15-2-2 combination works synergistically with acetone as a peeling agent [preferably 5% but over the possible range of 0.1% to 10%]. See Tables 1 and 2. for compositions and concentration ranges.

4. Hydroquinone screen cream is provided for application to areas of hyperpigmentation or generally to darkly pigmented skin at a selected interval, between two and four times daily, preferably three times. An alternate embodiment includes a hydro-alcoholic vehicle at night with the hydroquinone screen used in the morning. This hydroquinone screen cream contains hydroquinone in the range of 0.1% to 2%, preferably 2% as a skin bleach in a non-comedogenic water based emulsion. Also provided in the hydroquinone screen cream is a broad spectrum [UVA and UVB] sunscreen, preferably octylmethoxycinnamate, and preferably about 7.5% and benzophenone-3, preferably about 1.5% and emollients and moisturizers.

5. Therapeutic balm for night-time use. After the peeling/exfoliating treatment, the therapeutic hydrocortisone balm is applied at night time, containing the well-known anti-inflammatory and anti-pruritic drug hydrocortisone in the concentration range 0.1% to 2.5%, preferably 1% in a hydrous base.

6. Moisturization and Ultraviolet light [UV] protection is provided for sensitive skin by applying a quick absorbing oil free emulsion which is light in consistency and does not have a heavy or oily base. Broad spectrum [UVA and UVB] protection is provided without the use of oxybenzone, lanolins, glycols, etc. The UV filters are Octyl Methoxycinnamate in the range of 1.5% to 7.5% and Menthyl Anthranilate in the range of 1% to 10% and the oil-free emulsion itself is a water-based emulsion comprised of a water-based vehicle and an ester-based emollient phase.

Hyper Pigmented Skin and Darkly Pigmented Skin—Maintenance Phase

1. Cleansing twice daily is provided by the soap-free cleanser during the maintenance phase. Cleansing is accomplished with a soap-free cleansing lotion as in the therapy phase, the cleanser being designed to cleanse efficiently without excessive drying or irritation of the skin.

2. The degreaser is applied twice daily to deep clean the skin and remove excess sebum, which may reduce the effectiveness of the treatment pads. The degreaser is a hydro-alcoholic solution containing acetone in the concentration range of 0.1% to 10% but preferably 5%.

3. Gentle twice daily peeling/exfoliation is accomplished by the use of the 5-2-2 treatment pad during the maintenance phase. The 5-2-2 pad contains glycolic acid [preferably 5%, but over a possible range of 1–20%], salicylic acid [preferably 2%, but over a possible range of 0.1% to 5%], and lactic acid [preferably 2%, but over a possible range of 0.1% to 20%]. The peeling/exfoliating agent combination is carried in a penetrating hydro-alcoholic vehicle containing acetone in the concentration range of 0.1% to 10% as a co-solvent to insure proper delivery of the peeling/exfoliating agent to the skin area to be treated. The 5-2-2 combination works synergistically with acetone as a peeling agent [preferably 5% but over the possible range of 0.1% to 10%]. See Tables 1 and 2 for compositions and concentration ranges.

4. Hydroquinone screen cream is provided for application at a selected interval, between two and four times daily, preferably three times to pigmented areas. An alternate embodiment includes a hydro-alcoholic vehicle at night with the hydroquinone screen used in the morning. This hydroquinone screen cream contains hydroquinone in the range of 0.1% to 2%, preferably 2% as a skin bleach in a non-comedogenic water based emulsion. Also provided in the hydroquinone screen cream is a broad spectrum [UVA and UVB] sunscreen and emollients and moisturizers.

5. Sun protector is applied in the morning for day time use via quick absorbing, oil-free emulsion for sensitive skin. Broad spectrum [UVA and UVB] protection is provided without the use of oxybenzone, lanolins, glycols, etc. The UV filters are Octyl Methoxycinnamate in the range of 1.5% to 7.5%, preferably 7.5% and Menthyl Anthranilate in the range of 1% to 10% and the oil-free emulsion itself is a water-based emulsion comprised of a water-based vehicle and an ester-based emollient phase.

Composite Skin—Therapy Phase

1. Cleansing twice daily is provided by the soap-free cleanser during the maintenance phase. Cleansing is accomplished with a soap-free cleansing lotion as in the therapy phase, the cleanser being designed to cleanse efficiently without excessive drying or irritation of the skin.

2. The degreaser is applied twice daily to deep clean the skin and remove excess sebum, which may reduce the effectiveness of the treatment pads. The degreaser is applied in the morning only to the areas of T-zone oiliness. The degreaser is a hydro-alcoholic solution containing acetone in the concentration range 0f 0.1% to 10% but preferably 5%.

3. 15-2-2 Treatment Pads contain the peeling/exfoliating agent combination glycolic acid [preferably 15%, but over the possible range of 1–20%], salicylic acid [preferably 2%, but over the possible range of 0.1% to 5%], and lactic acid [preferable 2%, but over a possible range of 0.1% to 20%]. The peeling/exfoliating agent combination is provided in a penetrating hydro-alcoholic vehicle containing acetone as a co-solvent to insure proper delivery of the peeling/exfoliating agent to the skin area to be treated. The 15-2-2 combination works synergistically with acetone as a peeling agent [preferably 5% but over the possible range of 0.1% to 10%]. See Tables 1 and 2 for compositions and concentration ranges.

4. After the peeling/exfoliating treatment, the therapeutic hydrocortisone balm is applied, containing the well-known anti-inflammatory and anti-pruritic drug hydrocortisone in the concentration range 0.1% to 2.5%, preferably 1% in a hydrous base.

5. Moisturizer and UV protection is applied via quick absorbing, oil-free emulsion for UV protection of combination skin during the day time, and is applied in the morning after cleansing. Broad spectrum [UVA and UVB] protection is provided without the use of oxybenzone, lanolins, glycols, etc. The UV filters are Octyl Methoxycinnamate in the range of 1.5% to 7.5% and Menthyl Anthranilate in the range of 1% to 10%.

Composite Skin—Maintenance Phase

1. Cleansing twice daily is provided by the soap-free cleanser during the maintenance phase. Cleansing is accomplished with a soap-free cleansing lotion as in the therapy phase, the cleanser being designed to cleanse efficiently without excessive drying or irritation of the skin.

2. The degreaser is applied twice daily to deep clean the skin and remove excess sebum, which may reduce the effectiveness of the treatment pads. The degreaser is applied in the morning only to the areas of T-zone oiliness and in the evening to the entire face or other skin area to be treated. The degreaser is a hydro-alcoholic solution containing acetone in the concentration range of 0.1% to 10% but preferably 5%.

3. Gentle twice daily peeling/exfoliation is accomplished by the use of the 5-2-2 treatment pad during the maintenance phase. The 5-2-2 pad contains glycolic acid [preferably 5%, but over a possible range of 1–20%], salicylic acid [preferably 2%, but over a possible range of 0.1% to 5%], and lactic acid [preferably 2%, but over a possible range of 0.1% to 20%]. The peeling/exfoliating agent combination is carried in a penetrating hydro-alcoholic vehicle containing acetone in the concentration range of 0.1% to 10% as a co-solvent to insure proper delivery of the peeling/exfoliating agent to the skin area to be treated. The 5-2-2 combination works synergistically with acetone as a peeling agent [preferably 5% but over the possible range of 0.1% to 10%]. See Tables 1 and 2 for compositions and concentration ranges.

4. After the peeling/exfoliating treatment, the therapeutic balm is applied in the evening, containing the well-known anti-inflammatory and anti-pruritic drug hydrocortisone in the concentration range 0.1% to 2.5%, preferably 1% in a hydrous base.

5. Sun protector is applied in the morning for day time use via quick absorbing, oil-free emulsion for sensitive skin.

Broad spectrum [UVA and UVB] protection is provided without the use of oxybenzone, lanolins, glycols, etc. The UV filters are Octyl Methoxycinnamate in the range of 1.5% to 7.5% and Menthyl Anthranilate in the range of 1% to 10% and the oil-free emulsion itself is a water-based emulsion comprised of a water-based vehicle and an ester-based emollient phase.

TABLE 4

Individual Variation for the Treatment of Specific Skin Conditions
Therapeutic Phase - 5–14 Days, but Preferably 7 days
Maintenance Phase - 20–60 days, but Preferably 30 days
The Maintenance Phase is repeated as needed and may be followed by a repetition of the Therapeutic Phase When Needed AGING SKIN TREATMENT, PHOTO AGING SKIN and DRY SKIN

THERAPEUTIC PHASE

MORNING THERAPY
a. cleanse
b. sun screen
EVENING THERAPY
a. cleanse
b. degreaser
c. treatment pads
d. moisturizing anti-inflammatory hydrocoritsone therapeutic balm
MAINTENANCE PHASE MORNING MAINTENANCE
a. cleansing
b. degreasing
c. peel pads
d. sun screen
EVENING MAINTENANCE
A. cleansing
b. degreasing
c. peel pad
d. moisturizing anti-inflammatory hydrocoritsone therapeutic balm
TREATMENT OF SENSITIVE SKIN, THIN SKIN, ECZEMA

THERAPY PHASE

MORNING THERAPY
a. cleanse
b. moisturizing anti-inflammatory hydrocoritsone therapeutic balm
c. moisturizing sun screen
EVENING THERAPY
a. cleanser
b. degreaser, selected from the group consisting of
(1) non-acetone degreaser, comprised of ultra pure rehydrated aloe vera juice and a blend of sodium PCA and other humectants, such as methyl glyceth-20 in a water-based vehicle; and
(2) degreaser using a low concentration of acetone, i.e., a concentration of acetone substantially lower than otherwise disclosed in the present invention.
c. peel pads
d. anti-inflammatory composition.
MAINTENANCE PHASE MORNING MAINTENANCE
a. cleanser
b. degreaser, selected from the group consisting of
(1) non-acetone degreaser, comprised of ultra pure rehydrated aloe vera juice and a blend of sodium PCA and other humectants, such as methyl glyceth-20 in a water-based vehicle; and
(2) degreaser using a low concentration of acetone, i.e., a concentration of acetone substantially lower than otherwise disclosed in the present invention.
c. peel pads
d. moisturizing sun screen
EVENING MAINTENANCE TABLE 4-continued Individual Variation for the Treatment of Specific Skin Conditions
Therapeutic Phase - 5–14 Days, but Preferably 7 days
Maintenance Phase - 20–60 days, but Preferably 30 days
The Maintenance Phase is repeated as needed and may be followed by a repetition of the Therapeutic Phase When Needed a. cleanser
b. degreaser, selected from the group consisting of
(1) non-acetone degreaser, comprised of ultra pure rehydrated aloe vera juice and a blend of sodium PCA and other humectants, such as methyl glyceth-20 in a water-based vehicle; and
(2) degreaser using a low concentration of acetone, i.e., a concentration of acetone substantially lower than otherwise disclosed in the present invention.
c. peels pads
d. moisturizing anti-inflammatory hydrocoritsone therapeutic balm
ACNE TREATMENT

THERAPY PHASE

EVENING ACNE THERAPY TREATMENT
a. cleansing with soap-free non-detergent cleanser
b. degreasing
c. peeling pad
d. moisturizing anti-inflammatory hydrocoritsone therapeutic balm
MORNING ACNE THERAPY TREATMENT
A. cleansing with soap-free non-detergent cleanser
b. benzoyl peroxide 2.5% gel
c. sun screen
MAINTENANCE PHASE MORNING ACNE MAINTENANCE
a. cleansing with Anti-Bacterial cleanser
b. peeling pads
c. topical acne preparation, such as benzoyl peroxide
d. sun screen
EVENING ACNE MAINTENANCE
a. cleansing with Anti-Bacterial cleanser
b. peeling pads
c. topical acne preparation, such as benzoyl peroxide
d. moisturizing anti-inflammatory hydrocortisone therapeutic balm
HYPERPIGMENTED SKIN TREATMENT and DARKLY PIGMENTED SKIN

THERAPY PHASE

MORNING THERAPY PHASE
a. cleanser
b. hydroquinone screen [hydroquinone sun screen]
EVENING THERAPY PHASE
a. cleanser
b. degreaser
c. peeling pad
d. hydroquinone product in a sun screen vehicle or hydro alcoholic vehicle.
e. moisturizing anti-inflammatory hydrocoritsone therapeutic balm
MAINTENANCE PHASE MORNING MAINTENANCE
a. cleanser
b. degreaser
c. peeling pad
d. hydroquinone sun screen
EVENING MAINTENANCE
a. cleanser
b. degreaser
c. peeling pad
d. hydroquinone in hydroquinone sun screen or hydro-alcoholic vehicle.
e. moisturizing anti-inflammatory hydrocoritsone therapeutic balm

TABLE 4-continued

Individual Variation for the Treatment of Specific Skin Conditions
Therapeutic Phase - 5–14 Days, but Preferably 7 days
Maintenance Phase - 20–60 days, but Preferably 30 days
The Maintenance Phase is repeated as needed and may be followed by a repetition of the Therapeutic Phase When Needed

COMPOSITE SKIN TREATMENT

THERAPY PHASE

MORNING THERAPY
a. cleanser
b. degreaser, but only applied to oily areas of skin
c. moisturizing sun screen
EVENING THERAPY
a. cleanser
b. degreaser
c. peel pads
d. moisturizing anti-inflammatory hydrocoritsone therapeutic balm
MAINTENANCE PHASE MORNING MAINTENANCE
a. cleanser
b. degreaser
c. peel pads.
d. moisturizing sun screen
EVENING MAINTENANCE
a. cleanser
b. degreaser
b. peel pads
c. moisturizing anti-inflammatory hydrocoritsone therapeutic balm In summary, the present invention provides a novel home skin peel composition, method and kit for producing healthy and attractive skin.

Other modifications may be made to the present invention, without departing from the spirit and scope of the present invention, as noted in the appended claims.

I claim:

1. A composition for treating certain problem skin conditions, comprising aging skin, dry skin, photo aged skin, ache, eczema, thin skin, which occurs in women between the ages of 25 and 40, where skin thickness is reduced, Sensitive skin and composite dry-oily skin comprising:

a degreaser composition for use with a first cosmetic applicator pad, wherein the cosmetic applicator pad has pre-saturated therein said degreaser composition, and a peeling and exfoliating skin care composition for use with a second cosmetic applicator pad, wherein the cosmetic applicator pad has presaturated therein an effective concentration of said peeling and exfoliating skin care composition comprising from about 0.1 percent to about 20 percent by weight of at least one alpha hydroxy acid (excluding citric acid as a buffer) in combination with a suitable pharmaceutical vehicle for topical application of said peeling and exfoliating skin care composition to skin to be treated; and wherein the topical application of said skin peeling and exfoliating skin care composition is accomplished by wiping the cosmetic application pad presaturated with said skin peeling and exfoliating skin care composition on the skin to be treated and wherein topical application of said skin peeling and exfoliating skin care composition removes dirt, oil and dead skin cells and/or dead skin cell debris from the skin to be treated;

wherein said degreaser composition comprises:
Degreaser Composition
Materials are listed by Weight Percentages

| Material | From About | To About |
|---|---|---|
| Witch Hazel | 0.0 | 25% |
| Propylene Glycol | 0.0 | 25% |
| Camphor | 0.0 | 5% |
| Acetone | 0.0 | 10% |
| Alcohol | 0.1 | 80% |
| Sodium Borate | 0.0 | 1% |
| Purified Water | Balance of Composition to | 100.0% |

| Material | From About | To About |
|---|---|---|
| Disodium EDTA | 0.0 | 0.3% |
| Sodium Benzoate | 0.0 | 1.0% |
| Witch Hazel EO2 | 0.0 | 20% |
| Polysorbate-20 | 0.0 | 25% |
| Salicylic Acid USP | 0.0 | 5% |
| Alpha Hydroxy Acid USP (excluding citric acid as a buffer) | 0.1 | 20% |
| Ammonia, dissolved | 0.0 | 35% |
| Germall 115 | 0.0 | 1.0* |
| Acetone | 0.0 | 10% |
| Alcohol | 0.0 | 50% |
| Purified Water | Balance of Composition | 100.0%. |

2. The composition as in claim 1 wherein said peeling and exfoliating skin care composition further includes resorcinol of from about 0.1 percent to about 10 percent by weight.

3. The composition of claim 1 wherein said second peel and/or exfoliating composition is further comprised of salicylic acid in an amount of from 0.1 percent to 5 percent by weight.

4. The composition of claim 1 wherein said second peel and/or exfoliating composition is comprised of lactic acid in an amount of from 0.1 percent to 20 percent by weight.

5. The composition of claim 1 wherein said second peel and/or exfoliating composition is comprised of glycolic acid in an amount of from 0.1 percent to 20 percent by weight.

6. A composition for treating certain problem skin conditions, comprising aging skin, dry skin, photo aged skin, acne, eczema, thin skin, which occurs in women between the ages of 25 and 40, where skin thickness is reduced, sensitive skin and composite dry-oily skin comprising:

a degreaser composition for use with a cosmetic applicator pad, wherein the cosmetic applicator pad has pre-saturated therein said degreaser composition, and a peeling and exfoliating skin care composition for use with the cosmetic applicator pad, wherein the pad also has presaturated therein an effective concentration of said peeling and exfoliating skin care composition comprising from about 0.1 percent to about 20 percent by weight of alpha hydroxy acid (excluding citric acid as a buffer) in combination with a suitable pharmaceutical vehicle for topical application of said peeling and exfoliating skin care composition to skin to be treated; and wherein the topical application of said skin peeling and exfoliating skin care composition is accomplished by wiping the cosmetic application pad presaturated with said skin peeling and exfoliating skin care composition on the skin to be treated and wherein topical application of said skin peeling and exfoliating skin care composition removes dirt, oil and dead skin cells and/or dead skin cell debris from the skin to be treated, wherein said degreaser composition comprises:

Degreaser Composition

Materials are listed By Weight Percentages

| Material | From About | To About |
|---|---|---|
| Witch Hazel | 0.0 | 25% |
| Propylene Glycol | 0.0 | 25% |
| Camphor | 0.0 | 5% |
| Acetone | 0.0 | 10% |
| Alcohol | 0.1 | 80% |
| Sodium Borate | 0.0 | 1% |
| Purified Water | Balance of Composition to | 100.0%; | and wherein said peeling and exfoliating skin care composition comprises

Second peel and/or exfoliating composition

Materials are listed by Weight Percentages

| Material | From About | To About |
|---|---|---|
| Disodium EDTA | 0.0 | 0.3% |
| Sodium Benzoate | 0.0 | 1.0 |
| Witch Hazel EO2 | 0.0 | 20% |
| Polysorbate-20 | 0.0 | 25% |
| Salicylic Acid USP | 0.0 | 5% |
| Alpha Hydroxy Acid USP (excluding citric acid as a buffer) | 0.1 | 20% |
| Ammonia, dissolved | 0.0 | 35% |
| Germall 115 | 0.0 | 1.0% |
| Acetone | 0.0 | 10 |
| Alcohol | 0.0 | 50% |
| Purified Water | Balance of Composition | 100.0% |

7. The composition of claim 6 wherein said second peel and/or exfoliating composition is further comprised of salicylic acid in an amount of from 0.1 percent to 5 percent by weight.

8. The composition of claim 6 wherein said second peel and/or exfoliating composition is comprised of lactic acid in an amount of from 0.1 percent to 20 percent by weight.

9. The composition of claim 6 wherein said second peel and/or exfoliating composition is comprised of glycolic acid in an amount of from 0.1 percent to 20 percent by weight.

10. The composition as in claim 6 wherein said skin peeling and exfoliating composition further includes resorcinol of from about 0.1 percent to about 10 percent by weight.

11. A composition for treating certain skin conditions, comprising aging skin, dry skin, photo aged skin, ache, eczema, thin skin, which occurs in women between the ages of 25 and 40, where skin thickness is reduced, sensitive skin and composite dry-oily skin, comprising:

a peeling and exfoliating skin care composition for use with a cosmetic applicator pad, wherein the pad has saturated therein an effective concentration of said peeling and exfoliating skin care composition comprising from about 0.1 percent to about 20 percent by weight of alpha hydroxy acid (excluding citric acid as a buffer) in combination with a suitable pharmaceutical vehicle for topical application of said peeling and exfoliating skin care composition to the skin to be treated; and wherein the topical application of said skin peeling and exfoliating skin care composition is accomplished by wiping said cosmetic applicator pad presaturated with said skin peeling and exfoliating composition on the skin to be treated, and wherein topical application of said skin peeling and exfoliating skin care composition removes dirt, oil and dead skin cells and/or dead skin cell debris from the skin to be treated, and wherein said peeling and exfoliating skin care composition comprises:

materials are listed by weight percentages

| Material | From About | To About |
|---|---|---|
| Disodium EDTA | 0.0 | 0.3% |
| Sodium Benzoate | 0.0 | 1.0% |
| Witch Hazel EO2 | 0.0 | 20% |
| Polysorbate-20 | 0.0 | 25% |
| Salicylic Acid USP | 0.0 | 5% |
| Alpha Hydroxy Acid USP (excluding citric acid as a buffer) | 0.1 | 20% |
| Ammonia, dissolved | 0.0 | 35% |
| Germall 115 | 0.0 | 1.0% |
| Acetone | 0.0 | 10% |
| Alcohol | 0.0 | 50% |
| Purified Water | Balance of Composition | 100.0% |

* * * * *